United States Patent [19]

Meilland

[11] Patent Number: Plant 5,683

[45] Date of Patent: Mar. 11, 1986

[54] ROSE PLANT-MEIFOTA VARIETY

[75] Inventor: Marie L. Meilland, Antibes, France

[73] Assignee: The Conard-Pyle Company, West Grove, Pa.

[21] Appl. No.: 571,202

[22] Filed: Jan. 16, 1984

[51] Int. Cl.[4] ..... A01H 5/00

[52] U.S. Cl. ..... Plt./18

[58] Field of Search ..... Plt./17-18

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided having fully double blossoms which are of an attractive pink coloration. The blossoms are produced in abundance and are of an attractive form. Since the new variety is exceptionally vigorous and a remarkably rapid grower, it is well adapted for the production of cut flowers while being grown under greenhouse cultivation.

18 Drawing Figures

Summary of the Invention

The new and distinct variety of Hybrid Tea rose plant of the present invention was created by artificial pollination wherein two parents were crossed which previously had been studied for the characteristics sought. Both the seed parent and the pollen parent were unnamed seedlings. The parentage of the pollen parent of the new variety can be summarized as follows:

[[MEIALFI×(MEGER×MEBAN)]×GOLDEN GARNETTE]×unnamed seedling.

The variety Golden Garnette from which the pollen parent was partially derived is the subject of U.S. Plant Pat. No. 1,898.

The seeds resulting from the above pollination were sown and 85 plantlets were obtained which were physically and biologically different from each other. Selective study resulted in the identification of a single plant of the new variety. The desirable qualities of the new variety have been confirmed through extensive testing and the importance of the new variety has been firmly established.

It was found that the new variety of Hybrid Tea Rose plant of the present invention possessed the following characteristics:

(a) an exceptionally vigorous upright growth habit, (b) the abundant formation of fully double blossoms having an attractive form which are of a dark salmon pink coloration, and (c) a very rapid growth rate which renders it well adapted for greenhouse cultivation.

The blossoms of the new variety are of long duration and the petals detach well.

The new variety has been found to undergo propagation by budding, grafting, and cuttings. The characteristics of the new variety have been found to be strictly transmissible by such asexual propagation.

The rose plant of the new variety has been designated the Meifota variety.

BRIEF DESCRIPTION OF THE PHOTOGRAPH

The accompanying photograph shows as nearly true as it is reasonably possible to make the same in a color illustration of this character, typical specimens of plant parts of the new variety. The rose plants of the new variety described herein were grown at Cannet des Maures, Var, France, in a greenhouse and were grafted on *Rosa indica* rootstock.

DETAILED DESCRIPTION

Figures 1, 2, 3, 4, 5, 6, 7, 8, 9, 10, 11, 12, 13, 14, 15, 16, 17, 18:
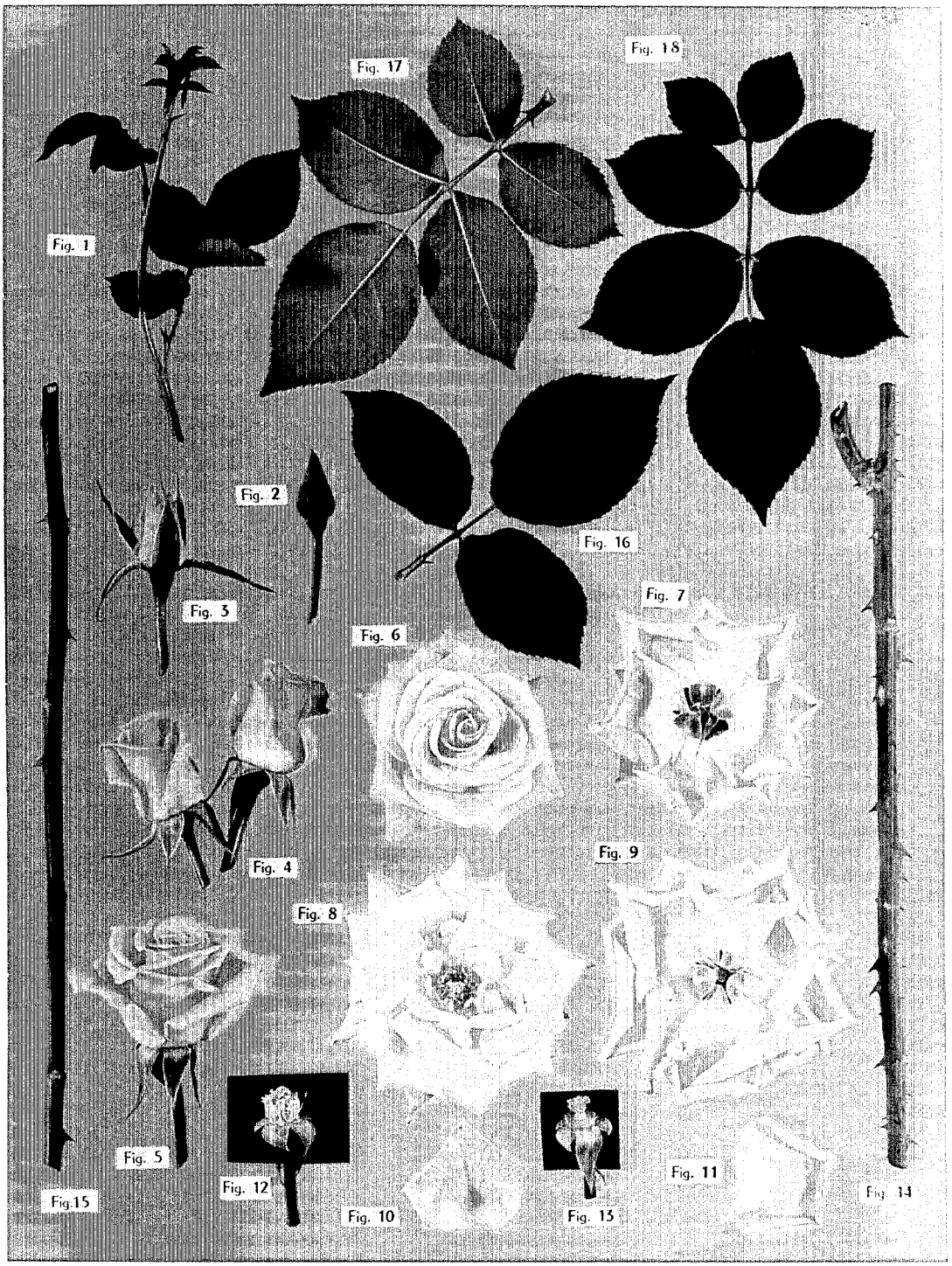
FIG. 1 illustrates a specimen of a young shoot.
FIG. 2 illustrates a specimen of a bud before the opening of the sepals.
FIG. 3 illustrates a specimen of a bud as the sepals begin to open.
FIG. 4 illustrates two bud specimens as the petals begin to open.
FIG. 5 illustrates a specimen of a flower at the beginning of opening.
FIG. 6 illustrates a specimen of a flower in the course of opening—plan view—obverse.
FIG. 7 illustrates a specimen of a flower in the course of opening—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a petal—upper side.
FIG. 11 illustrates a specimen of a petal—under side.
FIG. 12 illustrates a specimen of a floral receptacle showing the arrangement of the stamens (petals removed)
FIG. 13 illustrates a specimen of a floral receptacle showing the arrangement of the pistils (petals and stamens removed)
FIG. 14 illustrates a specimen of mature wood.
FIG. 15 illustrates a specimen of a young flowering stem.
FIG. 16 illustrates a specimen of a leaf with three leaflets—upper surface.
FIG. 17 illustrates a specimen of a leaf with three leaflets—under surface.
FIG. 18 illustrates a specimen of a leaf with seven leaflets—upper surface.

The chart used in the identification of the colors is that of The Royal Horticultural Society (R.H.S. Colour Chart). The terminology preceding the numbered references has been added to designate in common terms, the corresponding colors, Class: Hybrid Tea Plant:

*Height.*—When plants are pruned to 85 cm., flower-bearing stems of approximately 60 to 65 cm. in length are produced. Accordingly, the plant commonly has a height of 1.45 to 1.5 meters.

*Habit.*—Erect.

Branches:

*Color.*—Young stems: bronzed green, Yellow-Green Group 146A, very lightly shaded with red on the young stems. Mature wood: bronzed green, Yellow-Green Group 146A.

*Thorns.*—Shape: Upper edge: Straight, inclined toward the base. Lower edge: Concave. Size: Medium. Quantity: Commonly thornless on upper portions of young stems with a moderate number on lower portions. Color: On young stems: Reddish. On mature wood: Straw colored.

Leaves:

*Stipules.*—Adnate, pectinate, quite large and straight.

*Petioles.*—Upper side: Grooved, reddish-brown on young foliage and medium green on mature foliage with quite glandular edges. Under side: Light green; small thorns are commonly present; and it is sometimes very slightly glandular.

*Leaflets.*—Number: 3 or 5 most often, and sometimes 7. Shape: Ovate with an obtuse base. Serration: Simple and regular. Texture: Leathery. General effect: Average quantity of foliage, dense, has a medium-dull cast. Color: young foliage: Upper surface: Dark green, Yellow-Green Group 147A, somewhat shaded with red on very young foliage. Under surface: Light green, Yellow-Green Group 148C. Color: Mature foliage: Upper surface: Dark green, Yellow-Green Group 147A. Under surface: Light green, Yellow-Green Group 148C.

Inflorescence:

*Number of flowers.*—Commonly one per stem.

*Peduncle.*—Straight and rigid, light green, thornless at top, becomes slightly glandular at the base, its length is approximately 6 cm. on the average.

*Sepals.*—Upper surface: Light green, very slightly glandular, exterior sepals have slightly glandular sides.

*Buds.*—Shape: Oblong before the sepals open. Length: Approximately 3.5 cm. on average (not including the calyx) at the opening of the sepals. Size: Rather small. Color: When opening: Upper side: Rose Clairet, Red Group 50B. Under side: Rose Spinelle, Red Group 54A.

*Flower.*—Form: Fully double. Diameter: Approximately 9 cm. on average. Color: When opening begins: Upper side: Orange-Red Group 35C. Under side: Red Group 37B. Color: When partially open: Upper side: Red Group 37A. Under side: Red Group 37B. Color: When fully open: Upper side: Red Group 37B, slightly shaded with Orange-Red Group 37C on the petal edges of external petals. Under side: Red Group 37B. Fragrance: Very slight. Vase-life: Long. Corolla: Petals: Texture: Very consistent. Form: Rounded with lateral sides reflexed. Number: Approximately 25 on average. Petal drop: Petals fall cleanly after the normal life of the bloom has ended. Stamens: Number: 91 on average. Anthers: Ochre colored and slightly tinted with fuscia in the center; situated beneath the level of the stigmas. Filaments: Yellowish in coloration, somewhat tinted with fuscia, irregular in height. Pistils: Number: Approximately 46 on average. Stigmas: Straw colored. Styles: Straw colored with fuscia tip, tomentose at the base and somewhat twisted. Receptacle: Light green and smooth, at the dehiscence of the anthers in longitudinal cross-section it is funnel shaped.

Development:

*Vegetation.*—Very vigorous.

*Blossoming.*—Very abundant.

*Forcing aptitude.*—Outstanding due to excellent growth rate.

*Disease resistance.*—Excellent.

I claim:

1. A new and distinct variety of Hybrid Tea rose plant, substantially as herein shown and described, characterized particularly by (a) an exceptionally vigorous upright growth habit, (b) the abundant formation of fully double blossoms having an attractive form which are of a dark salmon pink coloration, and (c) a very rapid growth rate which renders it well adapted for greenhouse cultivation.

* * * * *